(12) United States Patent
Lin

(10) Patent No.: US 7,546,838 B2
(45) Date of Patent: Jun. 16, 2009

(54) LARYNGEAL-MASK CONSTRUCTION

(76) Inventor: Bih-Chern Lin, 7F-3, No. 2, Lane 222, King-Long Rd., Neihu District, Taipei (TW)

( * ) Notice: Subject to any disclaimer, the term of this patent is extended or adjusted under 35 U.S.C. 154(b) by 461 days.

(21) Appl. No.: 11/192,088

(22) Filed: Jul. 29, 2005

(65) Prior Publication Data

US 2006/0027238 A1    Feb. 9, 2006

(30) Foreign Application Priority Data

Aug. 9, 2004    (TW) .............................. 93212646 U

(51) Int. Cl.
*A61M 11/00* (2006.01)
(52) U.S. Cl. .............................. 128/207.15; 128/207.14
(58) Field of Classification Search ............ 128/207.14, 128/207.15, 200.16, 200.26
See application file for complete search history.

(56) References Cited

U.S. PATENT DOCUMENTS

| | | | | |
|---|---|---|---|---|
| 5,297,547 | A * | 3/1994 | Brain .................... | 128/207.15 |
| 6,318,367 | B1 * | 11/2001 | Mongeon ............... | 128/207.15 |
| 6,830,049 | B2 * | 12/2004 | Augustine et al. ...... | 128/207.15 |
| 6,918,388 | B2 * | 7/2005 | Brain .................... | 128/200.26 |
| 7,096,868 | B2 * | 8/2006 | Tateo et al. ............ | 128/207.15 |
| 2002/0011249 | A1 * | 1/2002 | Augustine et al. ...... | 128/207.15 |
| 2002/0189618 | A1 * | 12/2002 | Augustine et al. ...... | 128/207.15 |

\* cited by examiner

*Primary Examiner*—Steven O Douglas

(57) ABSTRACT

A laryngeal-mask construction comprises a tube body passing through an external expanding portion at its one end, wherein said external expanding portion is triangularly shaped and configured with indentations at its both front sides and a stud on its front end, the said tube body extends and ends with a circular plate outlet; a hollow annular resilient support, which is also supported by a horse-shoe shape fenestrated plate bridging between the said hollow annular resilient support and the groove in the extending tube is defined to surround said external expanding portion; a pliant elastomeric beret, being sticky and tensile is used for enclosing said external expanding portion and said hollow annular resilient support, after inserting into the oral cavity of a patient, the device outlet is adapted to place closer to the larynx of the patient for achieving an effective seal and lessening the risk of aspiration.

11 Claims, 10 Drawing Sheets

LARYNGEAL-MASK CONSTRUCTION

BACKGROUND OF THE INVENTION

1. Field of the Invention

The invention relates to a laryngeal-mask construction, and in particular, to a laryngeal-mask construction characterized in that it has simple elements, is easy to assemble, and keeps a necessary bending curvature such that it can stick closer to the larynx of a patient. It also has an integrated internal element that supports the mask resulting in better sealing so that it can not only prevent leakage of respiratory gas but also can prevent insufflations into the esophagus. An additional element is incorporated inside the hollow cavity of the mask so that any gastric fluid would be contained and adsorbed if there is regurgitation unfortunately. It is suitable to use to establish airway in a patient that is anesthetized or to be anesthetized, and can be substitute for a facemask for breathing in a first aid.

2. Description of the Prior Art

The inventor of this application had disclosed a laryngeal-mask construction in U.S. Pat. No. 6,546,931, titled "A supraglottic airway structure specifically used for anesthesia", such as shown in FIG. 9, including a silicone mask B and a main tube seat A with diverging tube opening A1. The main tube seat A is fitted through the silicone mask B. The upper and lower faces of the silicone mask B are formed with perforations B1, B2. A rubber annular tube F having different diameters is implanted in the silicone mask at the equator thereof. A soft sleeve C is fitted on the silicone mask B. The inner diameter of the soft sleeve C corresponds to the profile of the main tube seat A. The soft sleeve C has an irregular profile corresponding to the configuration of inner side of the fauces. The soft sleeve C is pushed forward to make an upper tube opening of the main tube seat A protruding out of the soft sleeve C. An anesthetic gas intake tube E having an engaging flange is fitted through the diverging section of the main tube seat A and engaged therewith. A fine string D is used to tie up the soft sleeve C, main tube seat A and the intake tube E so as to prevent the soft sleeve C from detaching from the main tube seat A. The laryngeal mask is able to completely air-tightly seal the throat of a patient without leakage and over-compressing the mucous membrane of the throat.

Although the construction described above could achieve the purpose of an airway conduit, it has the following operational and structural disadvantages:

When the above mentioned supraglottic airway device is placed in the oral cavity of a patient, it tended to be folded back due to contact of the front edge of the laryngeal-mask with the posterior wall of the pharynx.

The above-mentioned device has a circular opening that tends to increase the difficulty in the alignment with trachea as it is inserted into the oral cavity of a patient.

1. Because the mask body in the above-mentioned device is supported by an elliptical solid tube, as the mask body is inserted into the pharyngeal cavity of a patient, its periphery will be in a position against the two tonsils on both sides of the patient's pharyngeal cavity, thereby as the device is moved forward or is removed, not only there will be increased discomfort to the patient, but also the rubber annular tube of the device could be deformed, and further, due to the asymmetric organization of the tonsils, pharyngeal muscle, and the like in the pharynx, the front end of the device will shift from the center position of the larynx.
2. When the device is inserted into the oral cavity of a patient, its mask body will contact with the protruded epiglottis of the patient, and might hurt the epiglottis as the mask body moves forth and back. In addition, the epiglottis tends to block up the front outlet of the tube, resulting into the blockage of the airway.
3. In the actual practice, although the tip of the mask body can be placed against the esophagus of the patient, due to the mostly asymmetrical anatomy of the patient and the deviation during insertion, even if the laryngeal mask can be inserted into a right destined position (i.e., the center of the larynx), it might be unable to stick tightly around the opening of the esophagus, resulting into the escape of the gas into the esophagus and the stomach during positive pressure breathing. Furthermore, the annular ring can support only the side walls of the mask. Without covering completely the anterior wall of esophageal sphincter, it is inadequate in preventing gastric insufflations or aspiration.
4. The above-mentioned device has a number of constitutional elements, and its assembly is cumbersome. Moreover, when it is combined with an auxiliary device for assisting the bending of the tube body, no place is provided for the stopping of the inserted auxiliary device, whereby the larynx is susceptible to injury if the auxiliary device protruded out of the mask body.

A construction disclosed in the U.S. Pat. No. 5,355,879 provided a laryngeal mask construction to achieve the purpose of loading the peripheral-cuff seal to the laryngeal inlet; however, it had limitation for the airway tube to get closer enough because of the intervening peripheral cuff. It might also increase the pressure at the back wall of the pharynx. Further, in a laryngeal mask construction disclosed in U.S. Pat. No. 5,878,745, a gastro-laryngeal mask features pliantly compliant construction of the distal half of the mask, wherein the mask is of generally elliptical configuration, with an inflatable peripheral cuff to seal and support the mask around the laryngeal inlet. A back cushion is inflatable to engage the back wall of the pharynx and thus to forwardly load the peripheral-cuff seal to the laryngeal inlet. An evacuation tube for external removal of a possible gastric discharge completes an evacuation or discharge passage contained within the mask and opening through the distal end of the peripheral cuff. Special provision is made for assuring integrity of the discharge passage within the flexible distal half of the mask, i.e., assuring against collapse of the distal-end half of the pliantly compliant evacuation tube in the distal region of the mask, such that inflation of the mask does not compromise viability of the evacuation tube by compressing pliantly compliant material of the evacuation tube during periods of mask inflation. The special provision also favors such collapse of the mask when deflated as to provide a leading flexible edge for piloting a safe and correct advancing insertional advance of the deflated mask in the patient's throat, in avoidance of epiglottis interference and to the point of locating engagement in the upper sphincter of the oesophagus.

The above-mentioned evacuation tube for external removal of a possible gastric regurgitation fluid was effective only when the distal mask tip is engaged tightly in the upper sphincter of the esophagus, which might not be the case in some patients. The evacuation tube was also too small that if there were any particulate materials in the regurgitation, it would block the tube and defeats its mechanism.

Moreover, this sort of construction is supposed to be used only in fasted patients whose gastric fluid will not exceed 50 ml. It needs only a mechanism to accommodate the less than 50 ml of possible regurgitation fluid in the mask body and to adsorb it so that it will not aspirate into the laryngeal inlet causing laryngeal spasm or damage to the lung.

Accordingly, in view of the foregoing deficiencies associated with the previous constructions, the inventor had devoted to improve it, and finally, after several trials and errors, has provided a laryngeal-mask construction characterized in that it has simple elements, is easy to assemble, and can maintain a desired bending curvature in its use such that it can stick closer to the larynx of a patient with better seal and less risk of aspiration.

SUMMARY OF THE INVENTION

One objective of the invention is to provide a laryngeal-mask construction characterized in that it can be deposited rapidly and accurately closer and against the target larynx without aversion of the tip.

Second objective of the invention is to provide a laryngeal-mask construction characterized in that it can comply with the pharyngeal structure and epiglottis such that it can reduce the injury to the pharynx and epiglottis of a patient during its use.

Third objective of the invention is to provide a laryngeal mask construction characterized in that it will prevent the epiglottis being obstructed in to the airway opening.

Fourth objective of the invention is to provide a laryngeal mask construction characterized in that it not only can retain a lateral force along its mask border but also can strengthen the membrane that cover the void at the anterior wall of the esophagus sphincter.

Fifth objective of the invention is to provide a laryngeal mask construction characterized in that it has a mechanism to accommodate and adsorb any gastric fluid that is unfortunately regurgitated into the mask cavity.

Sixth objective of the invention is to provide a laryngeal mask construction characterized in that it has simplified elements and is simple and easy to assemble.

Yet another objective of the invention is to provide a laryngeal-mask construction characterized in that it can connect optionally to an introducer safely to provide a curvature to facilitate insertion.

In order to achieve the above-described objectives, a laryngeal-mask construction provided by the invention comprises a tube body provided with an external expanding portion at its one end, wherein said external expanding portion has a shape like a cap with lateral indentations at the front sides and is provided with a stud on its front end. At the lower end of said tube body, an extension is formed by extending the tube body further and ends with a circular plate with a groove between the said expanding portion and the said circular plate. A horse-shoe-shape flexible plate made of fenestrated cork and unwoven fabric material is bridged between the said groove and a hollow annular resilient support. The said hollow annular resilient support provides as an elliptical body with a broad transverse bar and two anteriorly placed short vertical strips to strengthen the its integrity. A hole is also provided on the centre of the transverse bar. An elastomeric sheath, being sticky and tensile, shaped like a beret with a small hole at the top encloses the said external expanding portion together with the said hollow annular resilient support by dressing the tube through the said small hole to form a laryngeal-mask construction. After inserting into the pharyngeal cavity of a patient, this invention provides a laryngeal mask with an airway opening closer to the laryngeal inlet of the patient with more effective seal and less risk of aspiration.

BRIEF DESCRIPTION OF THE DRAWINGS

These features and advantages of the present invention will be fully understood and appreciated from the following detailed description of the accompanying drawings.

DETAILED DESCRIPTION OF THE PREFERRED EMBODIMENT

Figure 1:
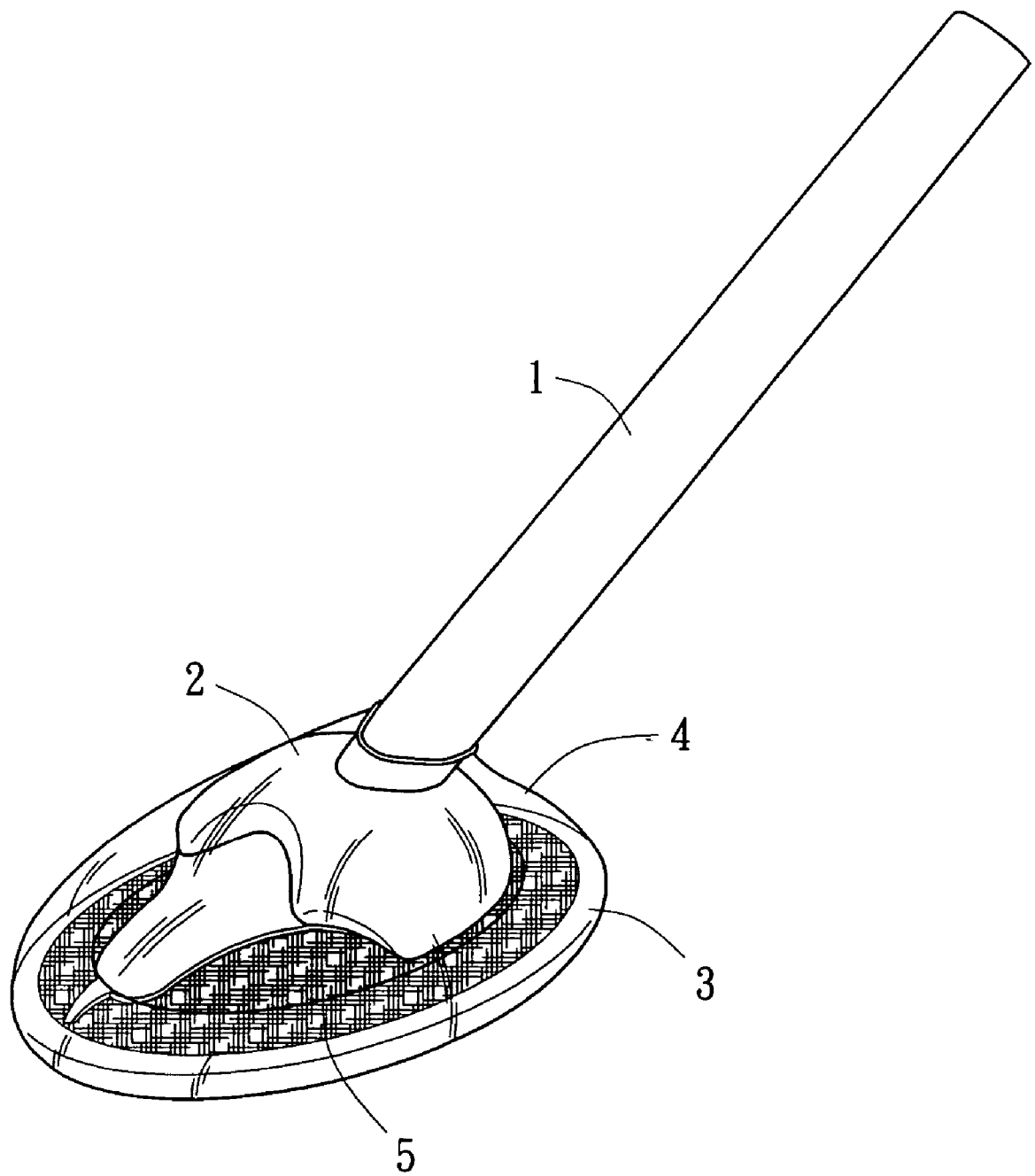
FIG. 1 is a three-dimensional outer view of a laryngeal-mask construction according to one embodiment of the invention.
Figure 2:
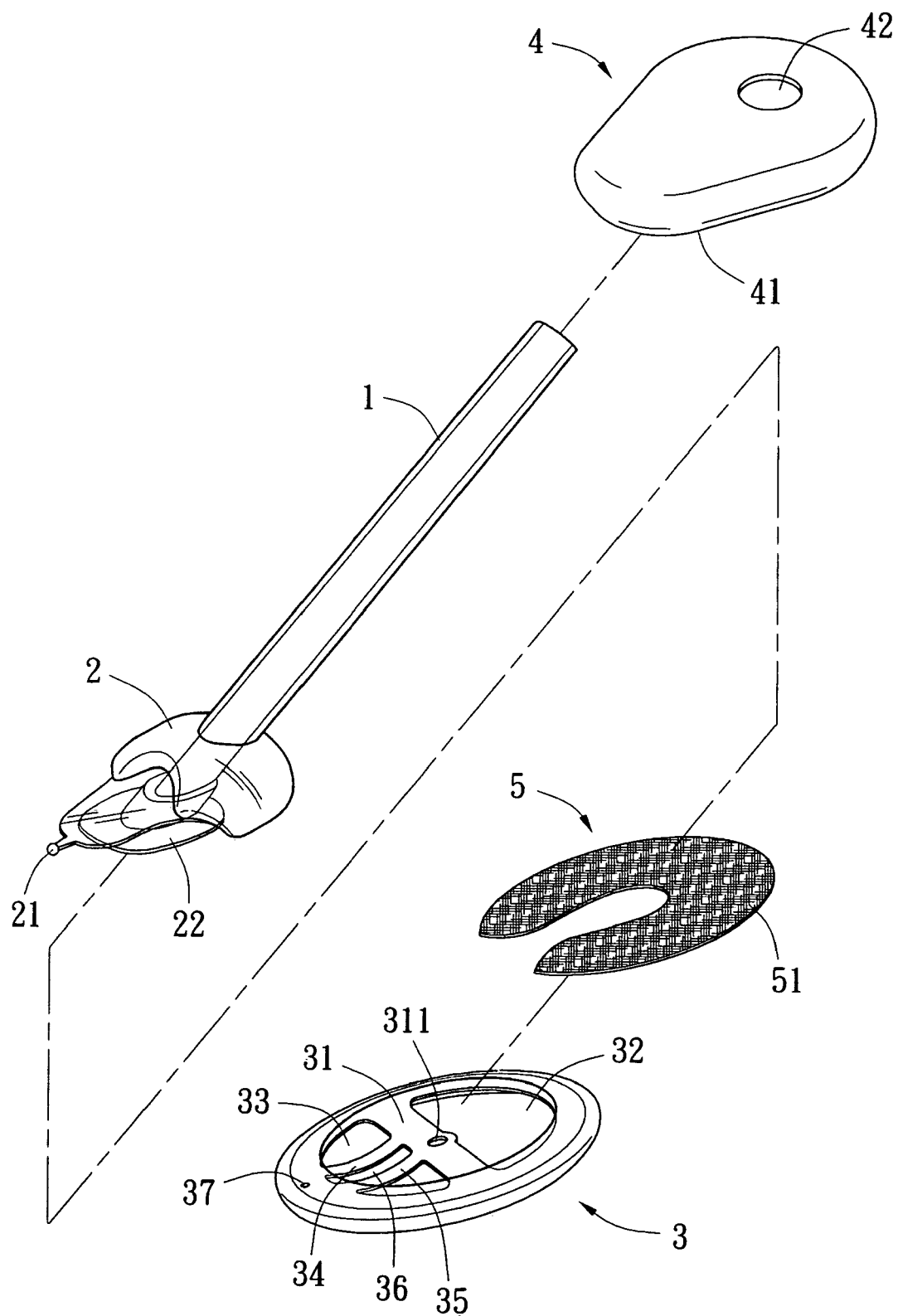
FIG. 2 is an elemental exploded view of a laryngeal-mask construction according to one embodiment of the invention.
Figure 3:
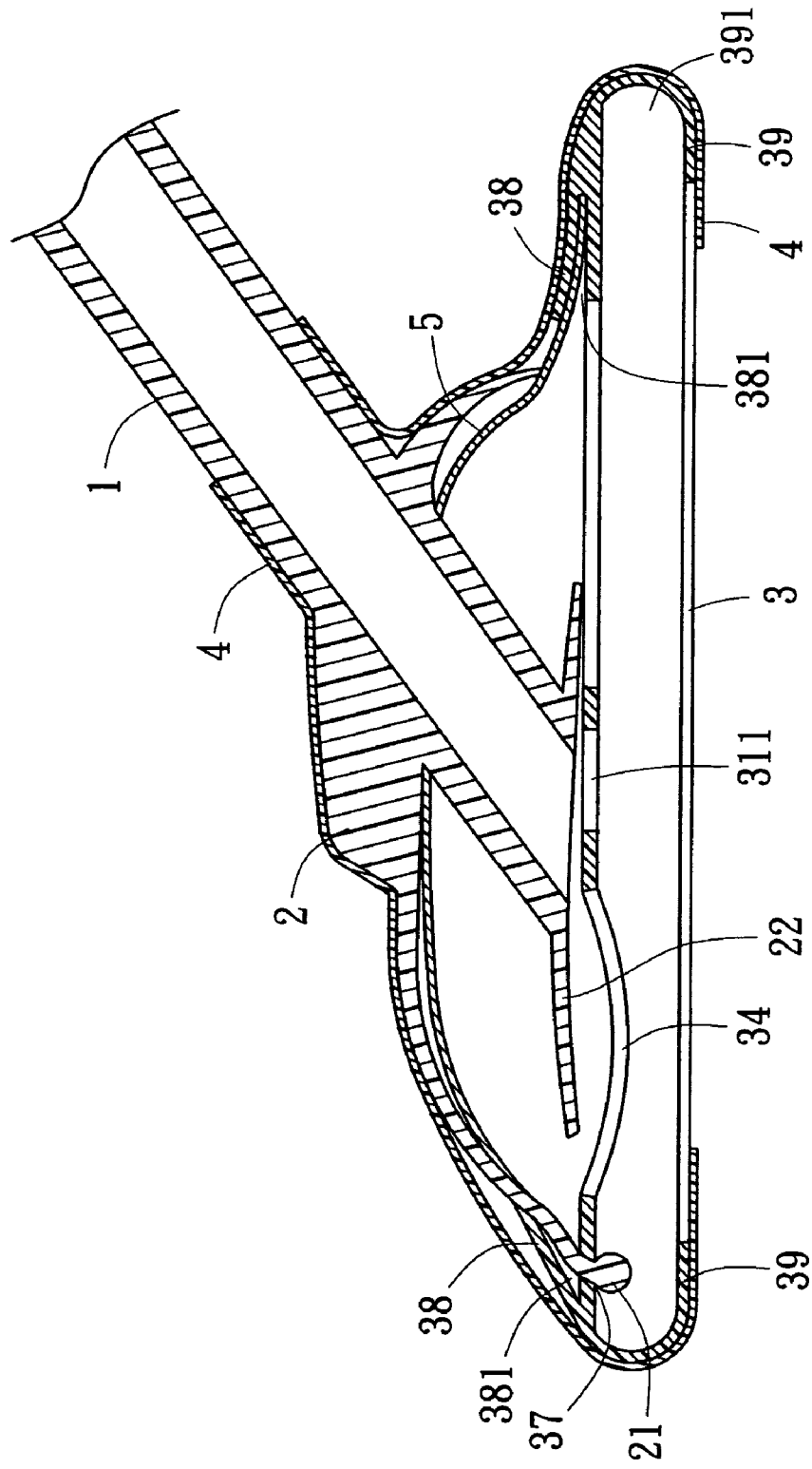
FIG. 3 is an exploded view showing the assembly of a laryngeal-mask construction according to one embodiment of the invention.
Figure 3A:
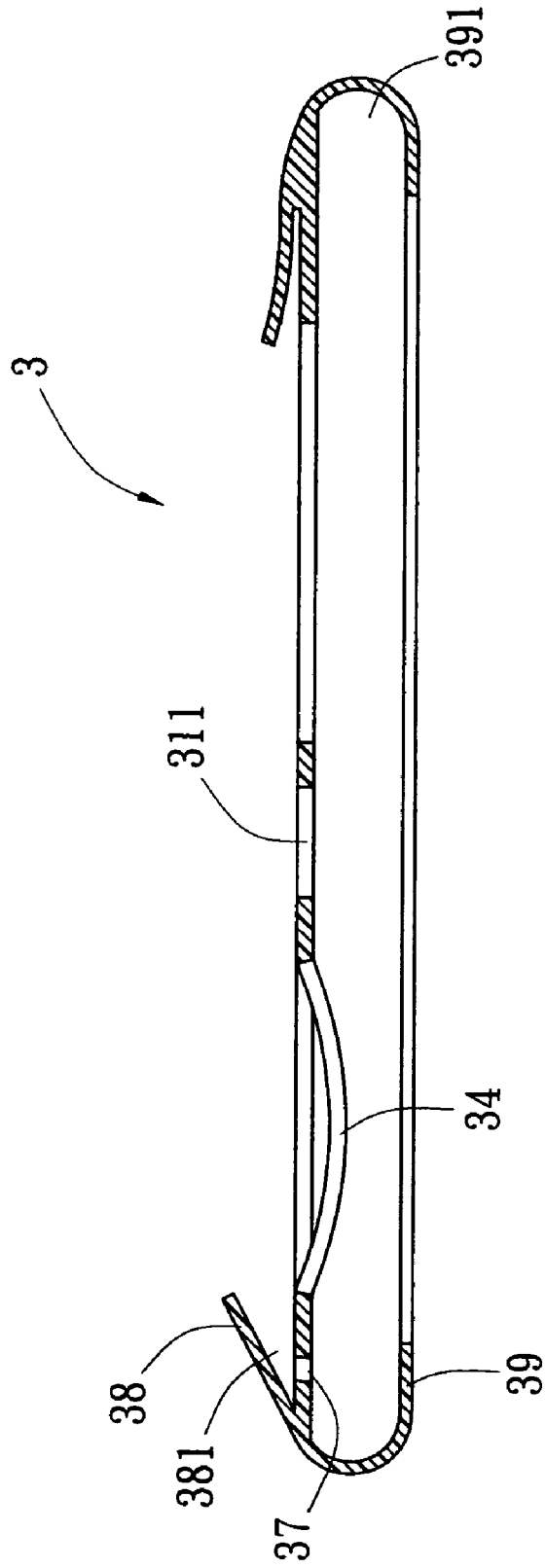
FIG. 3A is an exploded view showing the support in a laryngeal-mask construction according to one embodiment of the invention.
Figure 4:
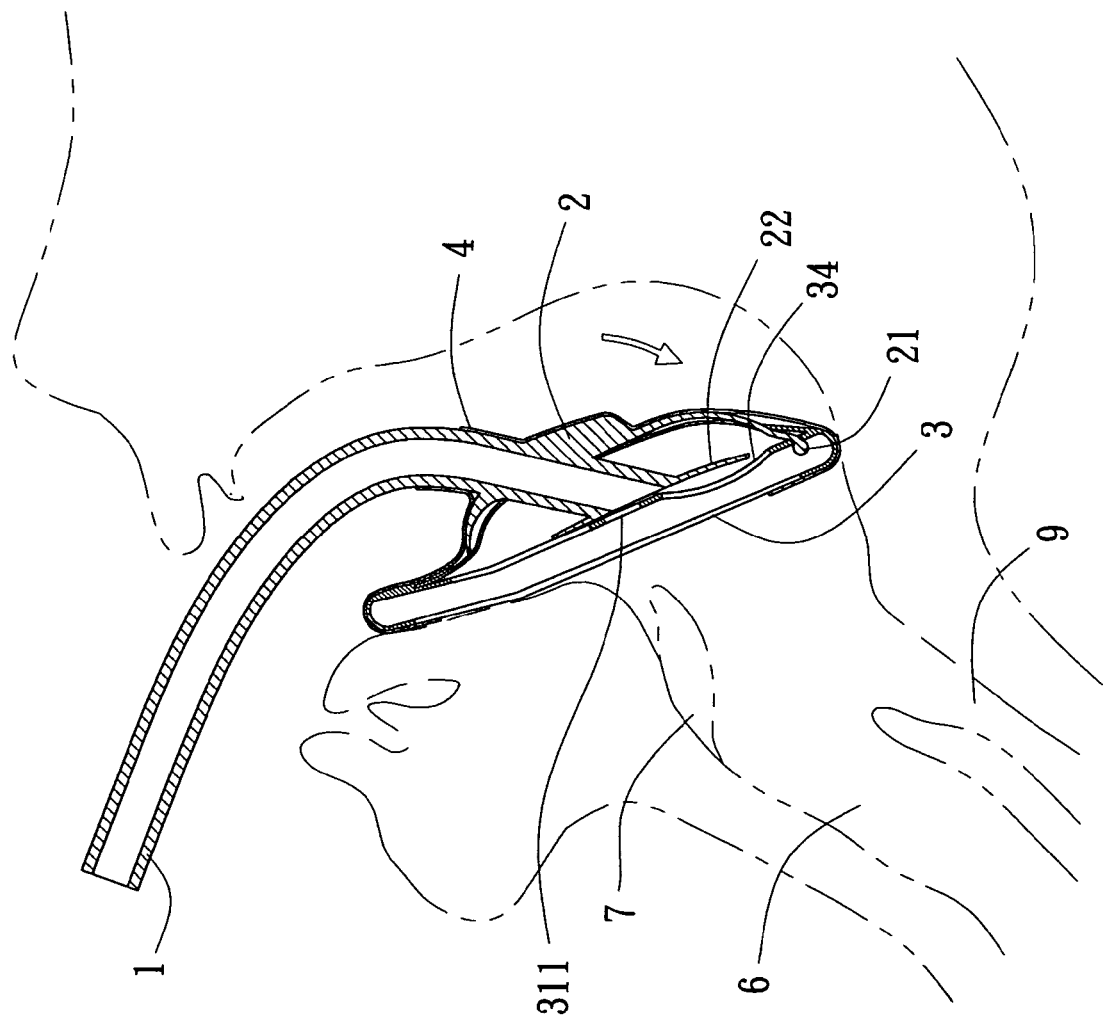
FIG. 4 is a schematic view showing the status of a laryngeal-mask construction according to one embodiment of the invention when it is inserted into an oral cavity.
Figure 5:
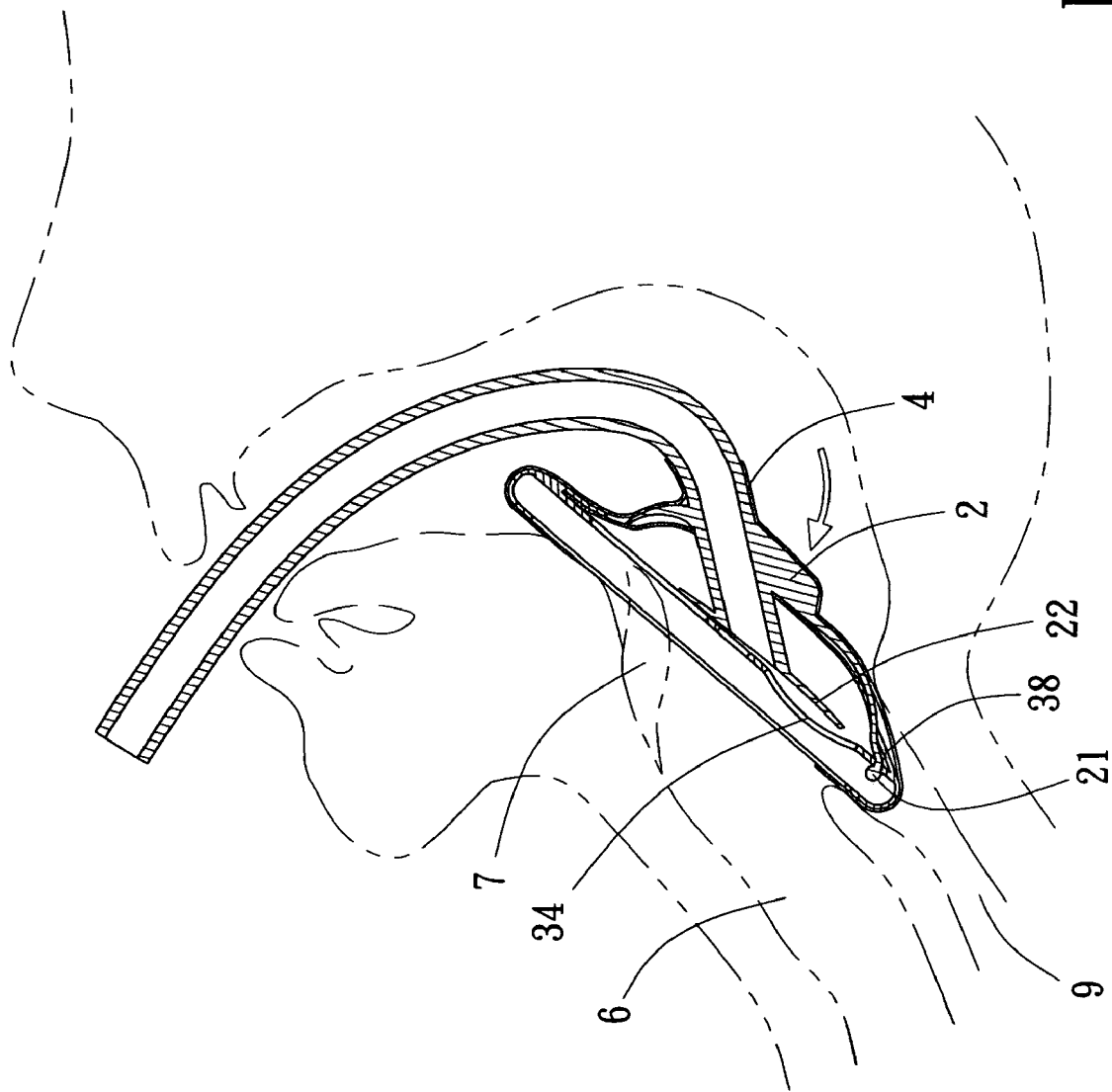
FIG. 5 is a schematic view showing the status of a laryngeal-mask construction according to one embodiment of the invention after it is inserted into an oral cavity.
Figure 6:
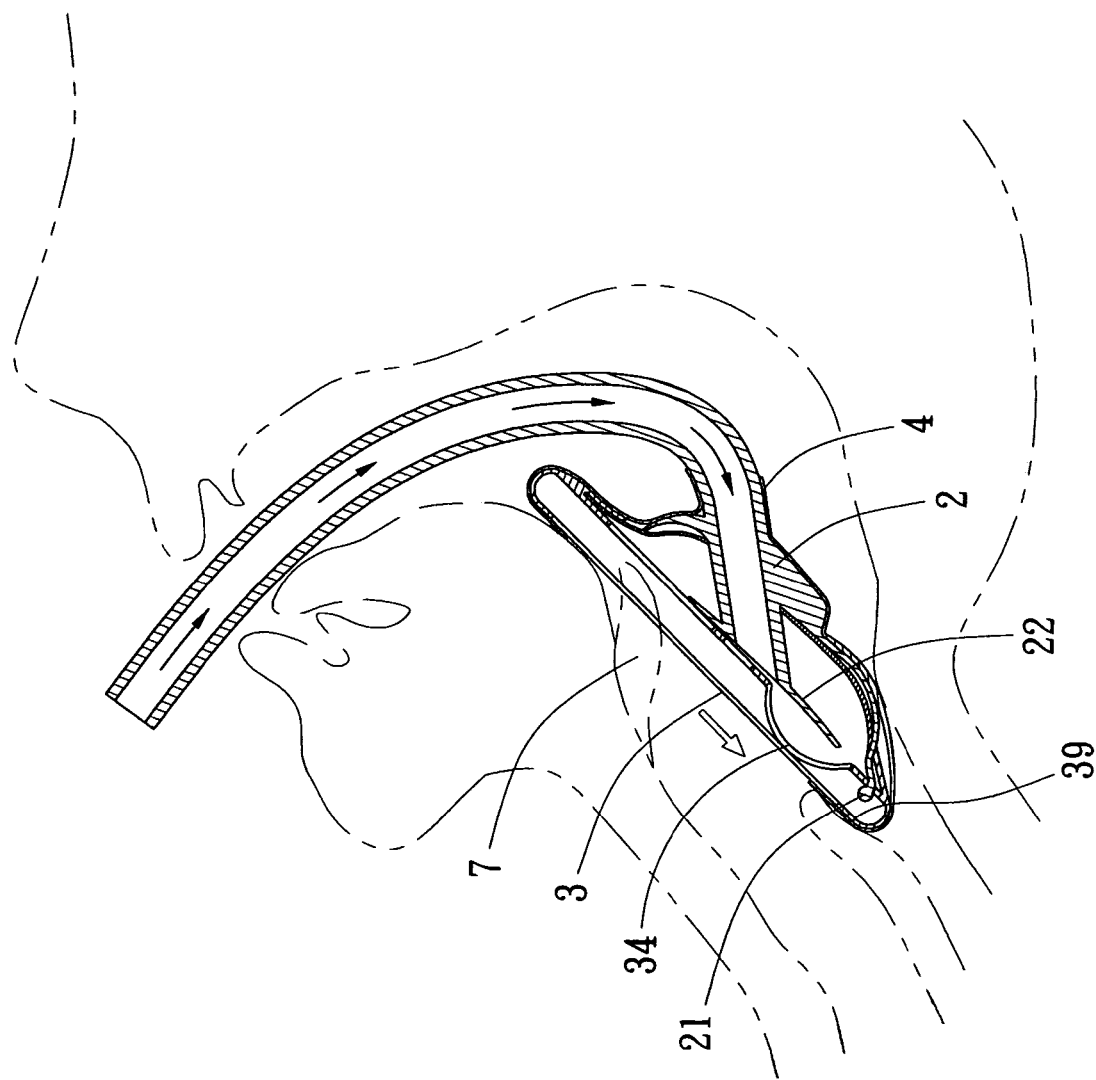
FIG. 6 is a schematic view showing the status of a laryngeal-mask construction according to one embodiment of the invention during ventilation.

Referring to FIG. 1-3A, a laryngeal-mask construction according an embodiment of the invention comprises primarily a tube body 1 provided with an external expanding portion 2 at its one end, wherein said external expanding portion 2 has a shape like a cap with indentations at its front sides and is provided with a stud 21 on its front end, while on the lower other end of said tube body 1, an extending tube which ends with a circular plate 22 is formed by extending there from; a hollow annular resilient support 3, provided for joining around said external expanding portion 2; a pliant elastomeric beret 4, being sticky and tensile, and useful for enclosing said external expanding portion 2 and said support 3 to form a laryngeal-mask construction that, after inserting into the oral cavity of a patient, can achieve the purpose of getting the distal airway opening closer to the larynx.

Wherein, said external expanding portion 2 is provided near the lower tube end of the tube body 1, and the lower tube end of the tube body 1 is an extending tube which ends in a circular plate 22. A supporting horse-shoe-shape plate 5 provided additionally between said external expanding portions 2 and said extending tube 22. Said supporting horse-shoe-shape plate 5 made of cork material and unwoven fabric material 51 is fenestrated to adsorb fluid if there is regurgitation unfortunately.

Said hollow annular resilient support 3 is provided with a transverse bar 31 for separating said support 3 into a large opening 32 and a small opening 33. Said small opening 33 provides correspondingly two curved vertical strips 34, 35 between the peripheries of said support 3 and said transverse bar 31, and a long hole 36 aligned with trachea 6 is formed between said vertical strips 34, 35. A hole 311 useful for placing a fiberscope tip to observe the vocal cord if necessary is provided at the middle of the transverse bar 31. Further, a hole 37 is provided thereon the support 3 to be engaged with the stud 21 at the front edge of the external expanding portion 2 of the tube body 1. An upper and a lower folded edges 38, 39 are extended inwardly along the periphery of said hollow annular resilient support 3 in a manner that an upper and a lower fillisters 381, 391 are formed from said support 3 and said upper and lower folded edges 38, 39, thereby the external expanding portion 2 of said tube body 1 can be accommodated on the transverse bar 3 inside the upper fillister 381 of said support 3.

Said elastomeric beret 4 is roughly an ellipsoid and is provided with a large and a small through holes 41, 42 at its lower and upper sides, respectively, for fixing on the tube body 1. Further, on the edge of said lower and upper through holes 41, 42, thick edges are provided for increasing tightness. The pore size of the small through hole 42 is less than or equal to the diameter of the tube body 1. The sticky design of said pliant elastomeric beret 4 can allow the contact between said sheath and the inner side of the pharynx keeping adhesion for a certain period of time, for example, at least 12 seconds, during interrupted gas supply. While, under a pressure of 12~18 cm-$H_2O$, the said pliant elastomeric beret 4 can maintain a constant capacity to prevent gas leakage due to change of capacity. The capacity of said pliant elastomeric beret sustaining a pressure of 19~27 cm-$H_2O$ will not exceed 1.2-fold more than its capacity at a pressure of 12~18 cm-$H_2O$.

When assembling, referring to FIG. 1-3A again, the upper end of the tube body 1 is allowed to penetrate first through the large and small through holes 41, 42 of the pliant elastomeric beret 4 in a manner that the pliant elastomeric beret 4 is fixed over the upper side of the external expanding portion 2. Next, penetrating the stud 21 on the front edge of the external expanding portion 2 through the hole 311 on one end of those two transverse strips 34, 35 of the support 3 allows the extending tube 22 on the lower side of the external expanding portion 2 to deposit on transverse bar 31, while the external expanding portion 2 can be accommodated in the upper fillister 381 of the support 3. At last, the pliant elastomeric beret 4 provided above the external expanding portion 2 is turned downwardly to enclose the external expanding portion 2 together with the support 3, while the periphery of the large through hole 41 on the pliant elastomeric beret 4 is turned outwardly to cover the lower folded edge 39 of the support 3.

Accordingly, as shown in FIG. 2, 4, 5, and 6, when an assembled mask body is inserted into the oral cavity of a patient, due to the presence of a stud 21 on the front edge of the external expanding portion 2, the front edge of the laryngeal mask can move downwardly along the posterior wall of the pharynx, and the curved external expanding portion 2 can be compressed inwardly after it contacts two tonsils to facilitate the forward movement of the mask body. The long hole 36 between the two vertical strips 34, 35 can be aligned readily with the trachea 6 such that gas can be supplied to the patient along tube body 1 and said long hole 36. Further, as the mask body contact the epiglottis 7, the epiglottis 7 can be suppressed by the extending tube with its circular plate 22 and the transverse bar 31, and can be accommodated in the large opening 32 so that the epiglottis 7 can be prevented from being hurt or blocking the tube opening. Once gas is supplied, the support 3 and the lower folded edge 39 at the front edge of the mask body can be supported by the gas due to the externally covered pliant elastomeric beret 4, which can efficiently further seal the esophagus 9 to prevent the escape of the gas. A physician can observe the vocal cord by a fiberscope that penetrates from the tube body 1 through the hole 311 at the middle of the transverse bar. In addition, the laryngeal mask construction can attach optionally at its rear side with a means such as, for example, an ambu bag to form a first aid breathing device, or an anesthesia machine to form a laryngeal mask to be used specifically for anesthesia.

Figure 7:
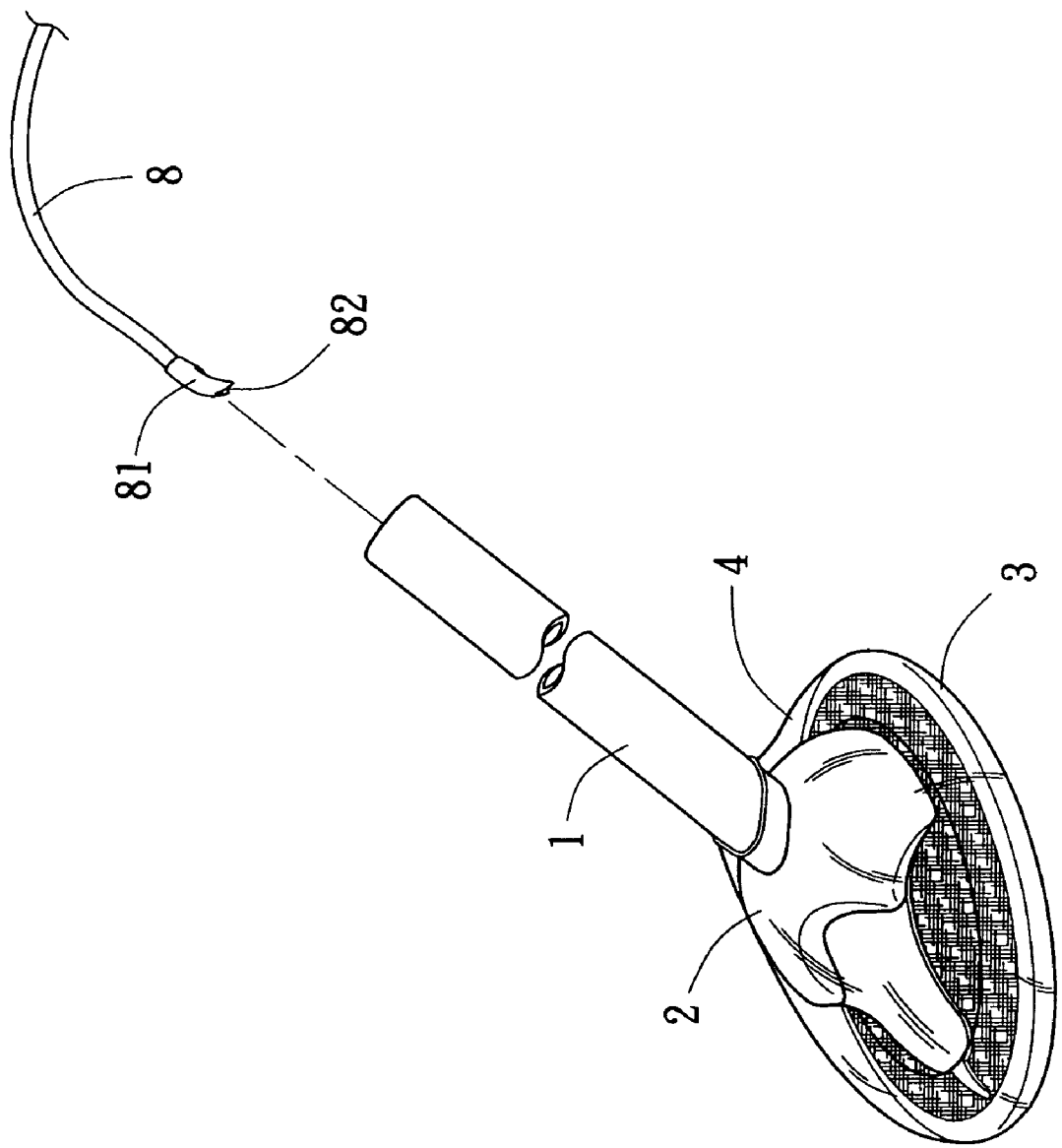
FIG. 7 is an elemental exploded view of a laryngeal-mask construction according to one embodiment of the invention equipped additionally with an auxiliary device.
Figure 8:
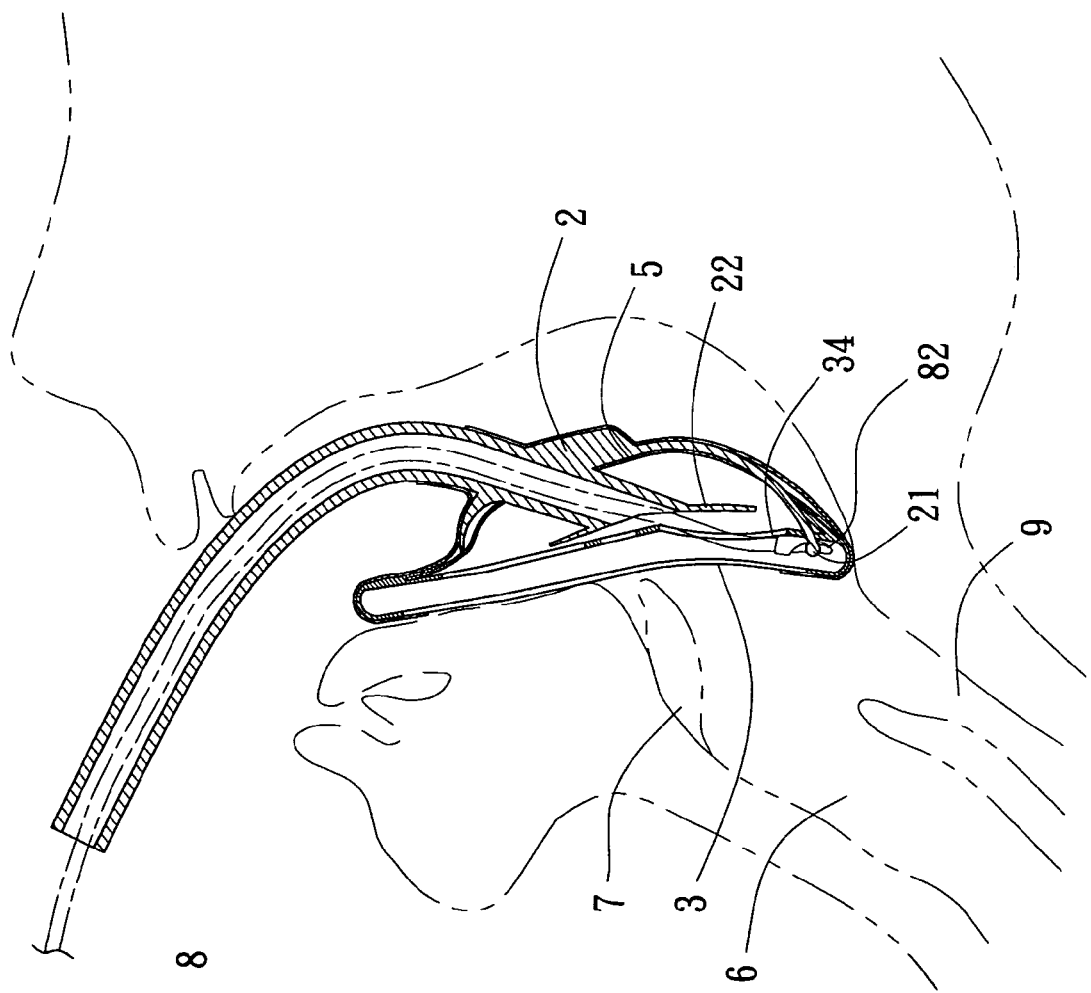
FIG. 8 is an exploded view showing the status in use of a laryngeal-mask construction according to one embodiment of the invention equipped additionally with an auxiliary device.
Figure 9:
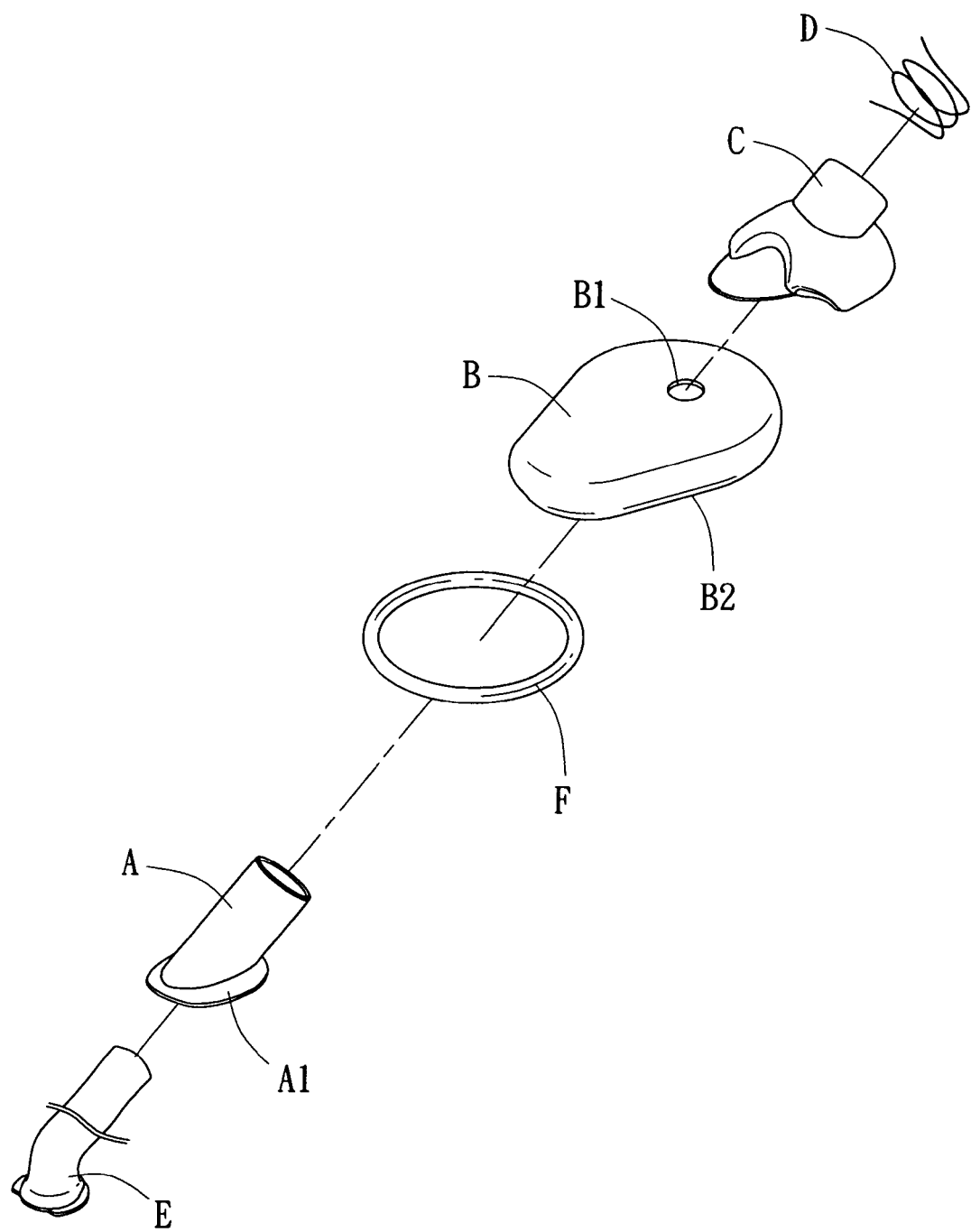
FIG. 9 is a three-dimensional exploded outer view of a conventional laryngeal-mask construction.

Furthermore, referring to FIG. 7 and 8, the present laryngeal mask construction can be combined with an auxiliary device to be used with a laryngeal mask for anesthesia as disclosed in the inventor's pre-patent publication no. 20030131845. Said auxiliary device 8 is a flexible rod provided at its one end with a soft sleeve 81. Said soft sleeve 81 is provided at the center of its front end with an open engaging hook 82 to be engaged with the stud 21 at the front end of the external expanding portion 2. When the laryngeal mask according to the invention is used for insertion, and the tube body 1 can be bended into a suitable curvature by means of the auxiliary device 8 in the tube body 1. With this, the laryngeal mask can be rapidly and conveniently inserted into the human oral cavity, and moves deeply in the pharynx avoiding in contact with the posterior wall of the pharynx.

The foregoing disclosure is intended to be illustrative of the invention and not limitative at any way of the scope thereof. Any change and modification apparent to the one skilled in the art will be considered as not departing from the subject matter of the invention.

Accordingly, the laryngeal mask construction provided by the invention has following advantages:

1. Since a stud is provided at the front end of the external expanding portion on the tube body of the inventive laryngeal-mask construction, when the laryngeal mask is entered in the oral cavity of a patient, the front edge of the laryngeal-mask can move downwardly along the posterior wall of the pharynx to prevent folding back of the mask body due to contact of with the posterior wall of the larynx.
2. In the laryngeal mask construction according to the invention, there are two curved vertical strips provided in the small opening correspondingly between the periphery of the support and the transverse bar, and a long hole aligned with the trachea is formed between said vertical strips, such that it is more convenient and easier to align with the trachea, and can be closer to the larynx.
3. The constitutive elements of the laryngeal mask construction according to the invention are relatively simple, and are readily to assemble. Once entering the oral cavity of a patient and contacting two tonsils, the space between the indented front sides of the external expanding portion and the hollow annular resilient support can be compressed inwardly to facilitate the movement of the mask body. In addition, the inventive laryngeal mask construction incorporates a supporting plate made of cork, and further, its annular support design has a transverse bar and two vertical strips, which can strengthen the structure of the inside of the laryngeal mask such that the laryngeal mask can stick tightly against the wall of the pharynx without deviation when the hollow annular resilient support rebound to its ellipsoidal shape after it passes the narrow passage between the two tonsils.
4. The annular resilient support constituted in the laryngeal mask construction according to the invention is provided with a transverse bar thereon in a manner that the support can be divided into a large and a small openings, thereby, when the mask body contacts the epiglottis of the patient, the epiglottis can be suppressed directly by the extending tube with the circular plate and the transverse bar, and is accommodated in the large opening so that the epiglottis can be prevent from injury and can be fixed to avoid blocking the tube opening.
5. The horse-shoe-shape plate not only strengthen the integrity of the mask body by anchoring inside the groove form by the end circular plate and extending tube but also provide an adsorbing medium for gastric fluid if regurgitation occur, through it wet-able nature and fenestration structure.

6. In the laryngeal mask construction according to the invention, pliant elastomeric beret is used to enclose the external expanding portion and the support into an integral body, and as a result, as gas is introduced, the support at the front of the mask body and the lower folded edge can be supported and hence block efficiently the esophagus to prevent gas from escaping. With the design of those two vertical strips in the support, in addition to the strengthening on the internal structure of the laryngeal mask, when the laryngeal mask bends due to contact with the posterior wall of the pharynx after entering the pharyngeal cavity, it will press those two vertical strips to the extent that those two vertical strips will seal tightly the membranous sheath of the elastomeric beret against the anterior wall of the upper esophageal sphincter, thereby the gas can be prevented from flowing into the esophagus.

7. Due to the hollow cavity of the mask body, there is enough space to accommodate fluid of less than 50 ml so that any regurgitation fluid will be contained in its cavity before effectively adsorbed by the horseshoe shape plate.

8. The laryngeal mask according to the invention can connect with a flexible auxiliary device to facilitate the bending of the tube body into a necessary curvature so that the mask body can be inserted conveniently and accurately towards a human larynx. Besides, a stud is provided at the front end of the external expanding portion such that not only it can be deposited by penetrating through the hole on the hollow annular resilient support for joining with the support, but also can engaged with the engaging hook at the front end of the soft sleeve provided on one end of said auxiliary device, thereby binding the auxiliary device and the mask body together to voiding the auxiliary device being protruded causing laryngeal injury.

9. In the laryngeal mask construction according to the invention, pliant elastomeric beret has stickiness and tensile force responsive for the expanding upon gas supply. The stickiness of the pliant elastomeric beret can allow the contact between said pliant elastomeric beret and the inner side of the pharynx to keep adhesion for a certain period of time (at least 12 seconds) during interruption of gas supply. While, under a pressure of 12~18 cm-H$_2$O, the pliant elastomeric beret can maintain a constant capacity, where the capacity of said pliant elastomeric beret sustaining a pressure of 19~27 cm-H$_2$O will not exceed 1.2-fold more than its capacity at a pressure of 12~18 cm-H$_2$O to prevent too much changes in capacity defeating the effective seal or causing pressure injury to the pharyngeal wall.

Many changes and modifications in the above-described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A laryngeal-mask construction comprises a tube body having a proximal and distal end and an external expanding portion in between, said external expanding portion is configured to be a triangularly shaped cap with indentations at its both front sides and is provided with a stud on its front end, while said distal end is defined to extend beyond said external expanding portion and end with a circular plate outlet; an annular resilient support is provided for joining around said external expanding portion; a pliant elastomeric beret, is used for enclosing said external expanding portion and said annular resilient support to strengthen the integrity of the device, after inserting into the oral cavity of a patient, an airway outlet is adapted to be closer to the larynx of a patient for achieving an effective seal and lessening the risk of aspiration.

2. A laryngeal-mask construction as claimed in claim 1, comprises further a horse-shoe-shape plate (5) provided between said external expanding portion (2) and said extending tube end with a circular plate (22) for strengthening the overall construction.

3. A laryngeal-mask construction as claimed in claim 1, wherein said annular resilient support (3) is provided with a transverse bar (31) for separating said support (3) into two parts, wherein an upper and a lower folded edges (38,39) are extended inwardly along the periphery of said support (3) in a manner that an upper and a lower fillisters (381,391) are formed from said support (3) and said upper and lower folded edges (38,39) thereby a lower portion of said tube body (1) is accommodated on the transverse bar (3) inside the upper fillister (381) of said support (3).

4. A laryngeal-mask construction as claimed in claim 3 wherein said annular resilient support (3) is divided by said transverse bar (31) into a large opening (32) and a small opening (33), wherein said small opening (33) provides correspondingly two curved vertical strips (34,35) between the periphery of said support (3) and said transverse bar (31), and a long hole (36) is formed there between said vertical strips (34,35) which is adapted to aligned with the tracheal (6) of a patient, wherein a hole (311) for fiberscopic observation is provided at the middle of the transverse bar (31), and wherein, thereon the support (3), a hole (37) is provided for the stud (21) at the front edge of the external expanding portion (2) of the tube body (1) to be engaged therewith.

5. A laryngeal-mask construction as claimed in claim 2, wherein said horse-shoe-shape plate (5) is made of cork like material covered with unwoven fabric (51) and is fenestrated.

6. A laryngeal-mask construction as claimed in claim 1, wherein said pliant elastomeric beret (4) is provided with through holes at its upper and lower sides, respectively for fixing on the tube body (1), and wherein, on the edge of said lower and upper through holes (41,42) thick edges are provided for increasing tightness.

7. A laryngeal-mask construction as claimed in claim 6, wherein said through holes provided on the pliant elastomeric beret (4) are a large and a small through hole (41,42), and wherein said pore size of the small through hole (42) is less than or equal to the diameter of the tube body (1).

8. A laryngeal-mask construction as claimed in claim 1, the stud (21) at the front end of the external expanding portion (2) when being engaged with the hole (37) provides a mean of anchorage for an auxiliary device that may be used optionally for insertion of the laryngeal mask.

9. A laryngeal-mask construction as claimed in claim 1, wherein said pliant elastomeric beret (4) is adapted to contact the inner side of the pharynx, while under a pressure of 12 to about 18 cm water and of 19 to about 27 cm water, said pliant elastomeric beret (4) is defined to maintain a tensile force to prevent too much change in its size.

10. A laryngeal-mask construction as claimed in claim 9, wherein said pliant elastomeric beret (4) is adapted to adhere to the inner side of the pharynx of a patient over a time period of at least 12 seconds when not under pressure.

11. A laryngeal-mask construction as claimed in claim 9, wherein the size of said pliant elastomeric beret (4), while sustaining a pressure of 19 to about 27 cm water, is defined not to exceed 1.2-fold more than its original size at the pressure of 12 to about 18 cm water.

* * * * *